(12) United States Patent
Mosimann (10) Patent No.: US 11,844,531 B2
(45) Date of Patent: Dec. 19, 2023

(54) BALANCING SYSTEM FOR A MICRO-SAW

(71) Applicant: BIEN-AIR HOLDING SA, Bienne (CH)

(72) Inventor: Samuel Mosimann, La Neuveville (CH)

(73) Assignee: Bien-Air Holding SA, Bienne (CH)

( * ) Notice: Subject to any disclaimer, the term of this patent is extended or adjusted under 35 U.S.C. 154(b) by 0 days.

(21) Appl. No.: 18/016,742

(22) PCT Filed: Sep. 2, 2021

(86) PCT No.: PCT/EP2021/074231
§ 371 (c)(1),
(2) Date: Jan. 18, 2023

(87) PCT Pub. No.: WO2022/049178
PCT Pub. Date: Mar. 10, 2022

(65) Prior Publication Data
US 2023/0190305 A1 Jun. 22, 2023

(30) Foreign Application Priority Data
Sep. 4, 2020 (EP) .................................... 20194548

(51) Int. Cl.
*A61B 17/14* (2006.01)
*A61C 1/10* (2006.01)
(Continued)

(52) U.S. Cl.
CPC .............. *A61B 17/144* (2016.11); *A61C 1/10* (2013.01); *A61C 1/181* (2013.01); *A61C 1/185* (2013.01);
(Continued)

(58) Field of Classification Search
CPC ........ A61B 17/144; A61B 2017/00345; A61B 2017/00398; A61B 2017/00477;
(Continued)

(56) References Cited

U.S. PATENT DOCUMENTS 3,642,002 A  2/1972 Otterstrom
4,036,236 A  7/1977 Rhodes, Jr.
(Continued)

FOREIGN PATENT DOCUMENTS

EP    2316356 A1   5/2011
WO   1997/010765  3/1997

OTHER PUBLICATIONS

International Search Report in PCT/EP2021/074231 dated Dec. 8, 2021, 5 pages.
(Continued)

*Primary Examiner* — Brooke Labranche
(74) *Attorney, Agent, or Firm* — Pearne & Gordon LLP (57) ABSTRACT

The present invention relates to a cutting device (1) for surgical or dental use, comprising a motor (10) connected to a handpiece (4) provided with a transmission module (2) for a cutting tool (3), the transmission module (2) comprising:
  a motor coupling part arranged to be set in rotation by the said motor (10);
  a kinematic chain transforming the rotary movement of the motor (10) into a first linear reciprocating movement (M1) of a blade holder (27) via a rotary transmission shaft (22) provided with an eccentric (23),
  the transmission module (2) being characterized in that it further comprises a counter-mass (5) arranged so as to move according to a second linear reciprocating movement (M2) synchronized with the first linear reciprocating movement (M1) of the blade holder (27), and in the opposite direction to the latter.

14 Claims, 8 Drawing Sheets

(51) Int. Cl.
*A61C 1/18* (2006.01)
*A61B 17/00* (2006.01)

(52) U.S. Cl.
CPC ............... *A61B 2017/00345* (2013.01); *A61B 2017/00398* (2013.01); *A61B 2017/00477* (2013.01); *A61B 2217/007* (2013.01)

(58) Field of Classification Search
CPC ..... A61B 2217/007; A61C 1/10; A61C 1/181; A61C 1/185
See application file for complete search history.

(56) References Cited

U.S. PATENT DOCUMENTS

| 5,725,530 A | 3/1998 | Popken |
| 10,201,334 B2 | 2/2019 | Gigon |
| 2015/0066032 A1 | 3/2015 | Young |

OTHER PUBLICATIONS

Written Opinion in PCT/EP2021/074231 dated Dec. 8, 2021, 9 pages.

BALANCING SYSTEM FOR A MICRO-SAW

TECHNICAL FIELD OF THE INVENTION

The present invention relates to the field of micro-saws intended for dental or surgical applications, i.e. handpieces provided with cutting tools. More specifically, it relates to a balancing module for such a micro-saw.

STATE OF THE ART

Motorized handpieces with an integrated motor generating a linear reciprocating movement of a saw are known; the product "Core Reciprocating Saw" from Stryker is an example of such a micro-saw provided with a reciprocating cutting tool carrying out reciprocating movements according to a course of approximately 3 mm and a frequency of between 10,000-30,000 revolutions per minute depending on the motor speed. This product was the object of a U.S. Pat. No. 4,036,236 which has now expired.

In this solution, the rotary motion of the motor is transformed into a reciprocal linear motion of a blade holder via a finger mounted on ball bearings oriented off-axis with respect to the transmission axis.

A disadvantage of this solution is the generation of a high level of vibrations that are transmitted directly to the practitioner's hand due to the large and periodic movement of the center of mass in the handpiece. In addition, the vibrations limit the cutting efficiency, which peaks with increasing speed and power applied to the motor; in fact, because of the increase in vibrations, the efficiency decreases with increasing power. The precision and speed of cutting are therefore limited by the displacement of the center of mass of the drive shaft-clamping-blade system.

In the surgical field, for cutting bones, saws are also known, e.g. from U.S. Pat. No. 5,725,530, which operate in the manner of a chain saw, i.e. based on one or more flexible belts provided with an abrasive toothing, and which are driven in rotation, e.g. in pairs, in opposite directions around fixed rigid guide parts. However, this solution is not suitable for high-precision operations involving small dimensions, and the configuration of the cutting tool also greatly reduces the tool's maneuverability.

Still in the surgical field, solutions are also known that use several blades driven in opposing movements to compensate for vibrations, such as, for example, the solution described in the international application WO97/10765. However, this solution is relatively complex to implement and is quite cumbersome in terms of the working area of the tool.

The patent document US2015/066032 further describes a cutting tool that is given both a low frequency reciprocating motion and very high frequency ultrasonic vibrations. A conversion element provided with oblique grooves in which drive pins are positioned allows a reciprocating motion to be imparted to a blade drive cylinder and jointly to a counterweight cylinder, respectively. A disadvantage of this type of tool, however, is that the integrated balancing device does not allow any decoupling between the motor part and that of the blade drive.

The solution disclosed in U.S. Pat. No. 3,642,002, which is much older, concerns a surgical tool provided with a connecting rod system connected to the rotor integral with a motor shaft, and in which the rotor is provided with a counterweight. A disadvantage of such a solution is that the counterweight is integrated directly into the motor part, which affects its performance and again prevents any modular configuration of the balancing device. There is therefore a need for a solution that is free of these known limitations.

SUMMARY OF INVENTION

An object of the present invention is to provide a new micro-saw for dental or surgical use in which the balancing is carried out in a simple and efficient way, and which also allows a decoupling of the motor part from the handpiece.

Another object of the present invention is to propose a new micro-saw for dental or surgical use with a minimum of space requirements, and requiring a minimum of adaptations compared with existing solutions.

According to the invention, these objects are achieved by a cutting device for surgical or dental use comprising a motor connected to a handpiece equipped with a transmission module for a cutting tool, the transmission module comprising:
 a motor coupling part arranged to be driven in rotation by the motor;
 a kinematic chain transforming the rotary motion of the motor into a first linear reciprocating movement of a blade holder via a rotary transmission shaft provided with an eccentric.

The transmission module is characterized in that it further comprises a counter-mass which is arranged in such a way as to move in a second linear reciprocating motion synchronized with the first linear reciprocating motion of the blade holder, and in the opposite direction to the latter.

One advantage of the proposed solution is that it reduces the level of vibration without requiring at the same time the implementation of a complex solution, nor creating significant additional space both in the handpiece and in the working area of the cutting tool.

Another advantage of the proposed solution is to offer a modular construction of a transmission-conversion system that guarantees both sufficient connection strength between the handpiece and the motor at the operational level, but also easy disassembly to use the motor part in combination with other surgical tools.

According to a preferred embodiment, the first kinematic chain of the transmission module comprises a first drive finger for the blade holder mounted on a first part of the eccentric, as well as a second drive finger for the counter-mass mounted on a second part of the eccentric.

An advantage of this solution is that it can be easily integrated into existing solutions, simply by doubling the fingers, and without having to create parallel transmission mechanisms for the counter-mass, which could be the source of parasitic vibrations, that do not effectively reduce the vibrations, but rather increase them.

According to an even more preferred embodiment, the eccentric is symmetrically arranged in a "V" shape, the first drive finger of the blade holder is mounted on a first series of bearings around the first part of the eccentric and the second drive finger of the blade holder is mounted on a second series of bearings around the second part of the eccentric.

An advantage of this solution is that it is possible to use a usual form of eccentric in the transmission kinematic chain and to simply add a second finger symmetrically mounted on a series of bearings to generate the reverse synchronized movement of the counter-mass. Thus, the integration of the counter-mass actuation system is made particularly simple on the same kinematic chain and with minimal space requirements.

According to another preferred embodiment, the geometrical shape of the counter-mass is adapted to that of the cutting tool and the blade holder, which gives maximum flexibility in the design of the balancing system. Preferably, the counter-mass will thus be cylindrical to correspond to a blade holder in the form of a shaft which is also cylindrical.

According to another preferred design, the counter-mass is guided axially along a transmission axis corresponding vectorially to the direction of longitudinal displacement of the blade holder and the cutting tool by at least one axial guide element inserted in at least one guide hole made in the counter-mass.

A technical advantage of this solution is that the vibrations generated by the back and forth movement of the cutting tool driven by the blade holder, which is usually also guided in this direction, can be compensated for as well as possible. The vibrations are thus confined to one and the same direction, and the self-balancing operation is easier without having to control interfering movements.

According to an even more preferred variant corresponding to this embodiment, the axial guide element is formed by a first axial guide rail and a second axial guide rail connecting in parallel a first frame part connected to the motor to a second frame part supporting and axially guiding the blade holder of the transmission module, the first axial guide rail and the second axial guide rail being inserted in respective guide holes of the counter-mass.

The additional technical advantage of this variant is that, on the one hand, the guiding properties of the counter-mass can be maximized and, on the other hand, space can be freed up in the middle for accommodating a coupling shoe for the blade holder. In addition, the fact that the rails act at the same time as guide pins for the counter-mass and as a connecting element for the frame of the transmission module makes it possible to reduce the number of parts necessary for its realization, and thus to reduce manufacturing costs.

In yet another preferred embodiment, the cutting device for surgical or dental use according to the invention is characterized in that the transmission module also comprises a cooling device for the counter mass.

An advantage of this solution is that it makes it possible to optimize the balancing of the device obtained via the counter mass by minimizing the undesirable effect of heating resulting from friction when the kinetic energy of the overall system increases.

According to an even more preferred embodiment for realizing such a cooling device, the first axial guide rail comprises a first integrated cooling duct and/or the second axial guide rail comprises a second integrated cooling duct.

An advantage of this solution is that the cooling mechanism can be directly combined in the guiding elements, which minimizes the overall size of the system and thus does not require a dedicated part to perform this additional technical cooling function, which is performed by elements directly integrated in the frame and which thus makes it possible to simultaneously perform other functions.

In yet another preferred embodiment, the transmission module is detachably connected to the motor, and the weight of the counter-mass is determined so as to be greater than a minimum value defined in relation to the combined weight of the blade holder and the cutting tool as a function of the force of disconnection of the transmission module from the motor, the course of the cutting tool, and the frequency of oscillation of the reciprocating motion of the cutting tool.

In another preferred embodiment, the weight of the counter-mass is determined to be less than a predefined value determined by a heat balance.

One advantage of each of these two solutions is that they make it possible to define counter-masses whose weight is not necessarily equal to, but preferably less than, the assembly formed by the cutting tool and the blade holder. It is thus possible to reduce the dimensions of this counter-mass and to minimize the overall dimensions of such a self-balancing system, while maximizing the level of design of the system according to the needs, depending on whether one prioritizes, for example, the reliability of the motor coupling part in relation to the level of heating in use as a function of the operations to be performed.

Thus, according to another particularly preferable embodiment, the weight of the counter-mass is simply between 25% and 50% of the combined weight of the assembly formed by the blade holder and the cutting tool, which constitutes an optimum in terms of coupling reliability and heating in use.

According to yet another preferential embodiment, the density of the counter-mass is greater than 7000 kg per cubic meter, which further reduces the volume of the counter-mass and thus its bulk for a given weight, and consequently minimizes the level of friction and heating generated during use.

In yet another preferred embodiment, the motor coupling part of the transmission module consists of a fluted hole, which co-operates with a standard coupling nose of said motor comprising a series of grooves into which O-rings are inserted.

Such a configuration of the transmission module allows a coupling with any standard dental or surgical micromotor, without requiring any adaptations of the latter. Thus, the proposed solution solves any possible incompatibility problems that might have arisen.

Moreover, since the transmission module is compatible with any type of usual micromotor, and since a handpiece comprising such a transmission module can therefore be sold independently of the "motor" parts to which they can be easily coupled and decoupled, the present invention also relates to such handpieces provided with such transmission modules taken independently of the motor.

BRIEF DESCRIPTION OF THE DRAWINGS

Other advantageous features will become clearer from the following description of a particular embodiment of the invention given as a non-limiting example and represented by the attached drawings, in which.

DETAILED DESCRIPTION

Figure 1:
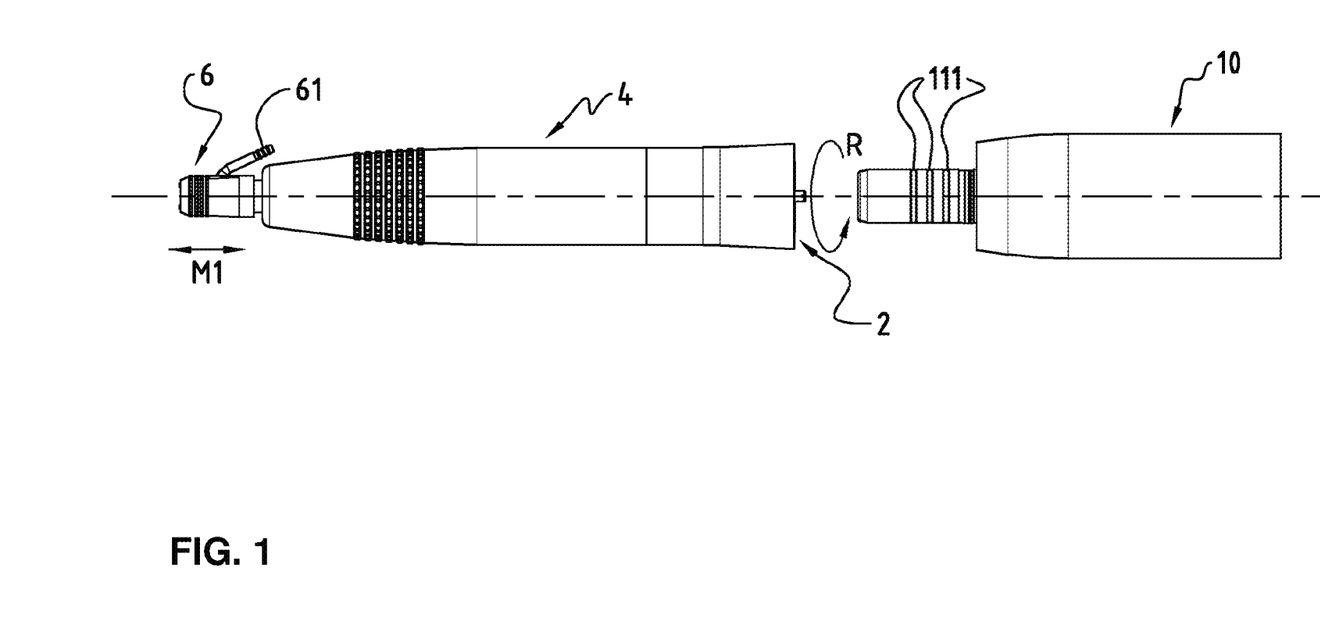
FIG. 1 illustrates a profile view of the functional parts of a surgical or dental cutting tool according to the present invention, namely the micromotor and the handpiece/micro saw.

FIG. 1 shows a side view of the functional parts of a surgical or dental cutting tool according to the present invention, and comprises, as for a conventional dental handpiece, a first part containing the motor and another constituting the handpiece itself, i.e. the part which is manipulated by the dental surgeon.

Figure 2A:
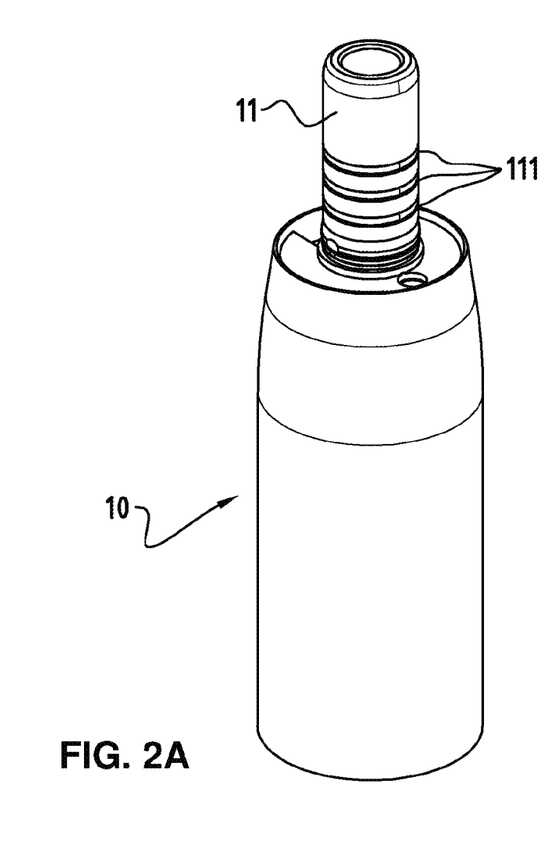
FIGS. 2A and 2B illustrate respectively a three-dimensional profile view of a common micromotor intended for dental or surgical applications as well as a sagittal sectional view of its coupling nose.
Figure 2B:
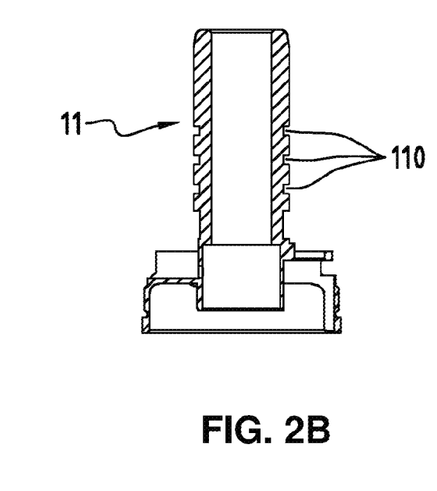

Thus, on the right-hand side of FIG. 1, the micromotor 10 can be distinguished, as well as its coupling nose 11 comprising, conventionally, a series of grooves in which are arranged O-rings for the transmission of a rotary movement indicated by the arrow R on this same figure. FIG. 2A shows such a micromotor 10 in perspective, and which resembles in all respects a usual micromotor 10 for a handpiece with a short coupling nose 11 on which are arranged O-rings 111 accommodated in the series of grooves 110 visible in FIG. 2B which shows the detail of the coupling nose in sagittal section.

On the left-hand side of FIG. 1, the handpiece housing 4, i.e. its outer casing, can be seen, enclosing the transmission module 2 described below. This transmission module 2 allows the rotary movement imposed at the entrance of the handpiece 4 to be transformed into a reciprocating movement M1 of a cutting tool, not shown in this figure, and which will be referred to in what follows as the "first" reciprocating movement M1 as corresponding to that of the blade holder 27, i.e. the element carrying the cutting tool 3. These two elements are further depicted in FIG. 3 showing an overview of the transmission and self-balancing mechanism according to a preferred embodiment for the present invention.

At the left end of the handpiece 4 is shown a clamping device 6 for the cutting tool 3, which is provided with a fin corresponding to an integrated irrigation channel 61 for supplying the surgically treated area 61 with physiological fluid, so as to minimize the heating of this area. The solution of coupling a cutting tool to a transmission mechanism as described, for example, in the applicant's European patent EP2316356 may, for example, be very suitable for mounting the cutting tool 3 within the scope of the present invention, and for this reason, no further details will be provided in the following regarding these aspects of attaching the cutting tool 3 to the transmission module 2 of the handpiece 4.

The modular construction thus proposed, with a handpiece 4 carrying the cutting tool 3 to form a micro-saw removable with respect to the micromotor 10, thus offers, on the one hand, the possibility of using the same surgical micromotor 10 not only in combination with the handpiece 4, but also with any other mechanical handpiece available in a hospital or medical practice (e.g. implantology contra-angles); on the other hand, it makes it possible to ensure a more efficient cleaning, decontamination and sterilization process of all the elements of the handpiece 4, in particular of the components in contact with the irrigation liquid, thus in indirect contact with the patient. In fact, the possibility of disconnecting the handpiece 4 from the motor allows for better manual cleaning of the handpiece 4 or the use of dedicated fixtures when cleaning in a washing machine or in a thermo-disinfector.

Figure 3:
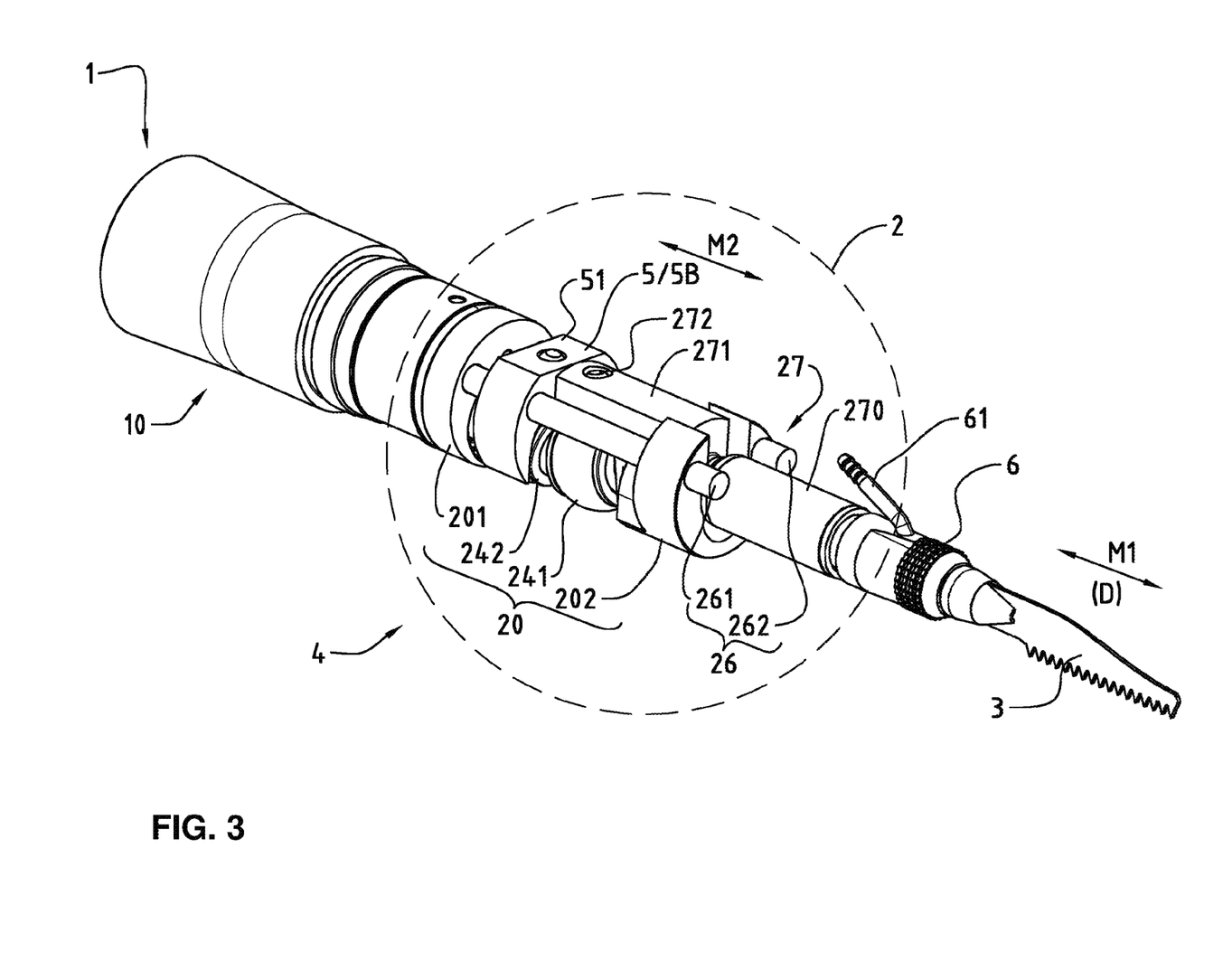
FIG. 3 is a perspective view of a cutting tool for surgical or dental use according to a preferred embodiment of the invention, provided with a transmission module balanced by a short counter-mass.

FIG. 3 illustrates in more detail the transmission mechanism according to a preferred embodiment of the invention, in which the counter-mass 5 used is a short counter-mass 5B, the purpose of which is thus to minimize friction and the generation of too much heat to achieve self-balancing. It consists of a three-dimensional perspective view of a complete assembly composed of the micromotor 10, assembled to a handpiece 4 whose casing has been removed in order to see the interior and in particular the transmission module 2, circled in dotted lines, which is intended to transmit the movement of the motor to the cutting tool 3 according to a first reciprocating movement M1 according to a predetermined course D.

The cutting tool 3 according to a reciprocating motion in translation is driven by a blade holder 27 and is attached to the latter via a clamping device 6 provided with an integrated irrigation channel 61 supplying the surgical treatment area with physiological fluid. The transformation of the rotational movement of the motor into a translational movement of the blade holder 27 is carried out via a first finger 241, the structure of which will be explained in detail with the aid of FIGS. 7*a* and 7*b*, and which is inserted into a first insertion hole 272 of a coupling shoe 271 provided for this purpose. The connecting part of the blade holder 27 between the coupling shoe 271 and the clamping device is in turn constituted by a cylindrical body 270.

As can be seen in FIG. 3, the transmission module comprises a frame 20 formed by a first part 201 for connection with the micromotor 10, and a second part 202 in the shape of a U and constituting the support of the blade holder 27. The first part 201 and the second part 202 are connected to each other by means of two cylindrical rods respectively, forming in parallel a first axial guide rail 261 and a second axial guide rail 262, constituting an axial guide element 26 for the counter-mass 5 (here the short counter mass 5B). In this way, the frame 20 can perform a guiding function for the counter-mass 5 without requiring the addition of a dedicated part. The short counter-mass 5B is driven in a second reciprocating motion M2, opposite to that of the first reciprocating motion M1 of the cutting tool, via a second finger 242 that is inserted into a second hole 51 of the counter-mass 5.

Figure 6:
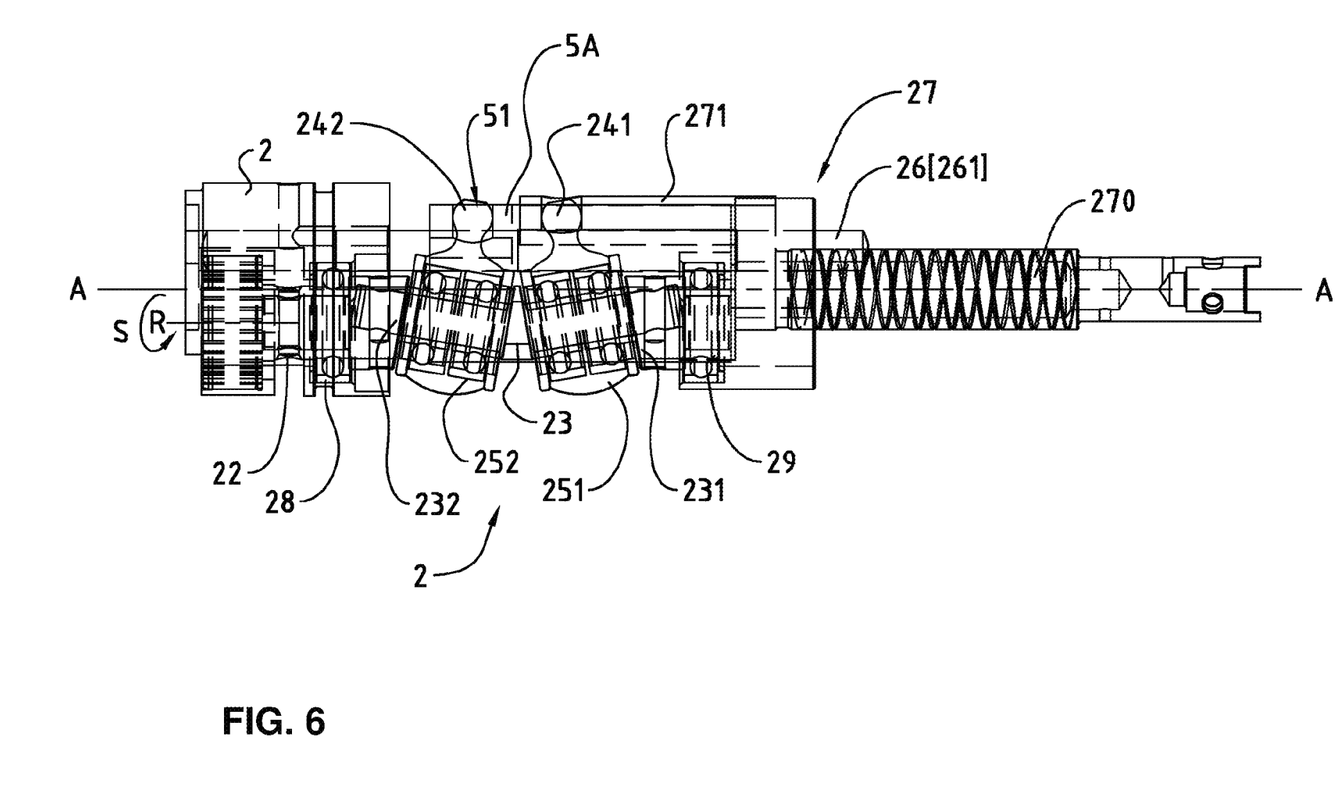
FIG. 6 is a sagittal section view of the transmission module shown in FIGS. 3 and 4.
Figure 7A:
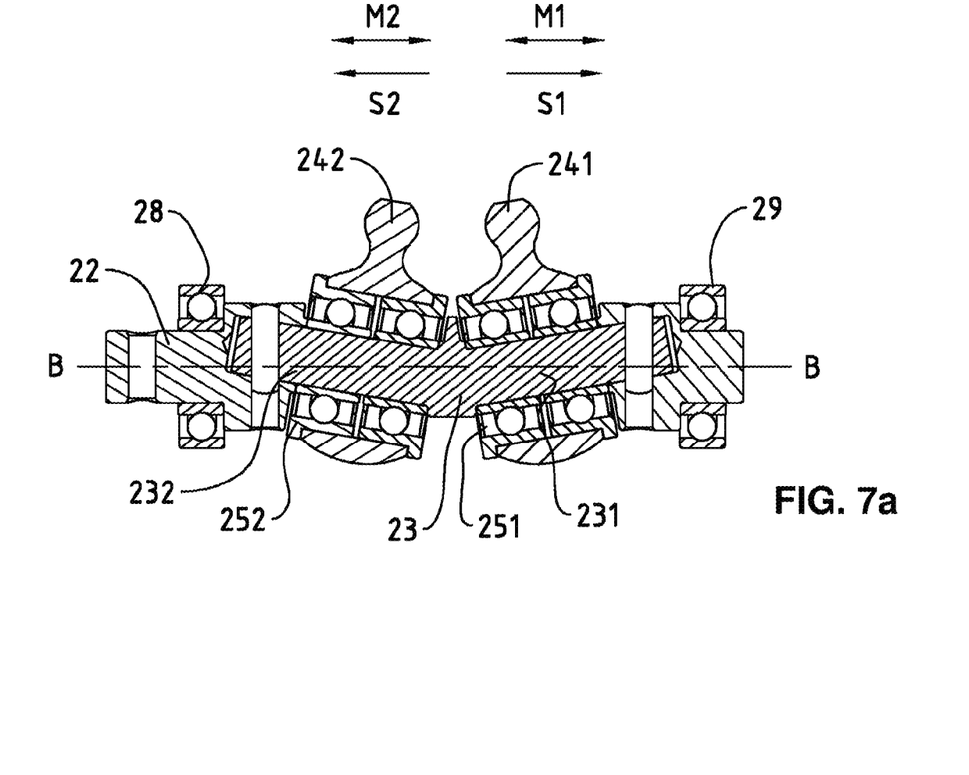
FIGS. 7A and 7B are respectively a top view and a sagittal section view of the transmission shaft, the eccentric and the fingers for the activation of the blade holder and the counter-mass respectively, according to the preferred embodiment described with the aid of the preceding figures.

Thus, compared with a prior art solution, self-balancing has been achieved simply by doubling the fingers, without having to substantially modify either the structure of the frame, the drive mechanism, and in particular the eccentric 23 illustrated in particular in FIGS. 6 and 7*a*/7*b*. This eccentric, which rotates around the same axis as that of the transmission shaft 22, generates a reciprocating translational movement of the end of the fingers while causing a movement respectively towards and away from their lower end due to the non-constant distance with respect to the axis of rotation all along the eccentric.

Figure 4:
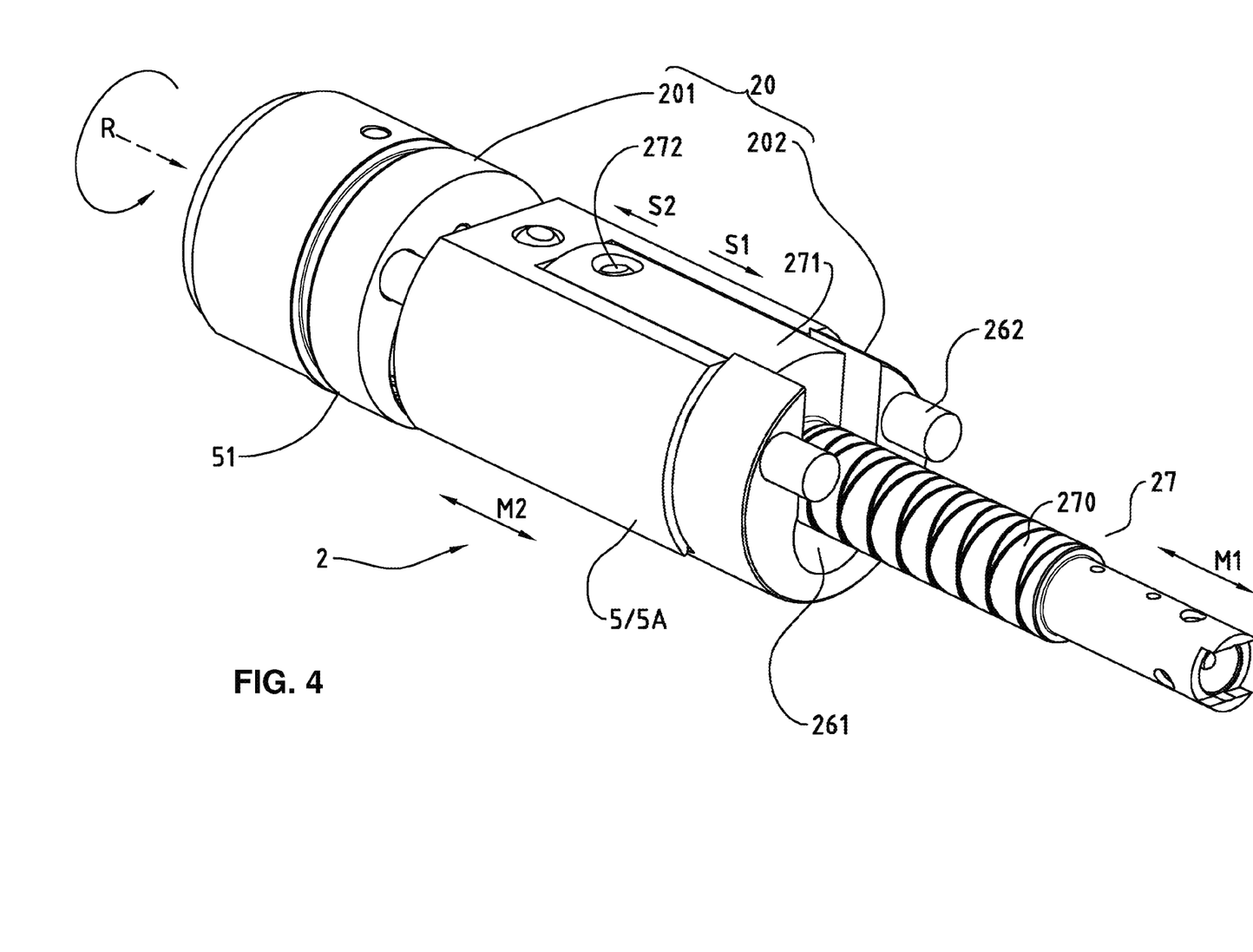
FIG. 4 is a perspective view of a transmission module for a cutting tool for surgical or dental use according to another preferred embodiment for the invention, in which the counter-mass is long.

FIG. 4 illustrates an enlargement of a transmission module 2 according to another preferred embodiment for the invention, this time using a long counter-mass 5A instead of the short counter-mass 5B shown in the previous FIG. 3. The other parts illustrated in this figure are identical in all respects to those in FIG. 3 and will not be re-described in detail. The transmission and balancing mechanism remains identical to that of the previous embodiment by allowing the first reciprocating motion M1 of the blade holder 27 to be generated from the rotary motion R supplied as input via the micromotor 10, and to generate in parallel a second reciprocating motion M2 of the long counter-mass 5A. The second reciprocating movement M2 of the counter-mass is synchronized in phase opposition with respect to the first reciprocating movement M1; these two movements M1 and M2 being always generated via a first finger 241 and a second finger 242, respectively, of which only the ends are visible, the rest being hidden under the long counter-mass 5A. The direction of movement of the first finger S1 is always opposite to that of the second finger S2.

Figure 5:
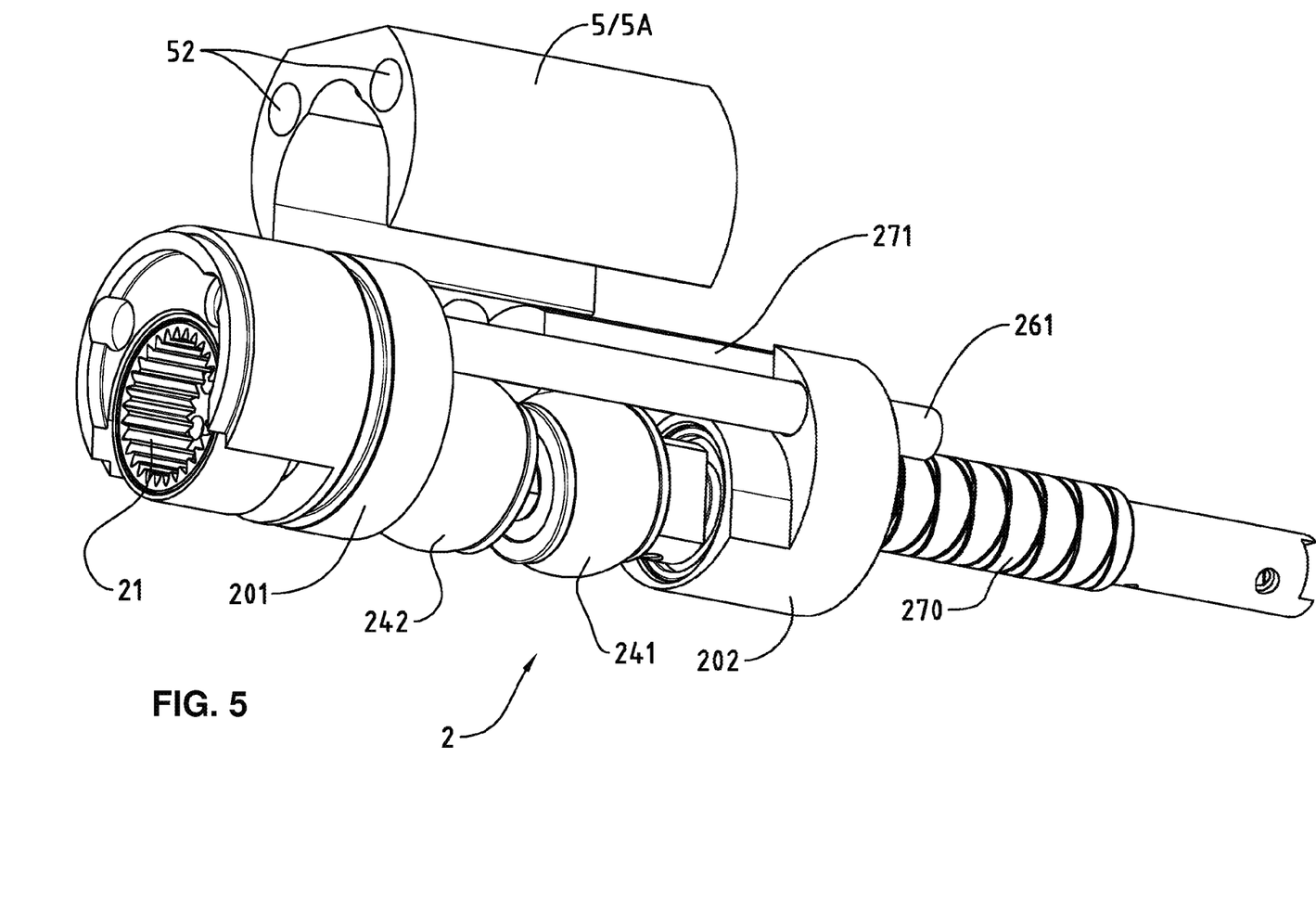
FIG. 5 is an exploded perspective view of the transmission module for a surgical or dental cutting tool according to the preferred embodiment of FIG. 3.

FIG. 5 is an exploded perspective view of the transmission module 2 for a cutting tool for surgical or dental use according to the preferred embodiment of the previous FIG. 4, i.e. having a long counter-mass 5A. The body of each of the drive fingers can now be seen, i.e. the first drive finger 241 of the blade holder 27, and the second drive finger 242 of the counter-mass 5A, which also has two longitudinal guide holes 52 allowing the respective insertion of each of the axial guide rails oriented parallel to the axis of displacement of the blade holder 27, whose cylindrical body 270 and the coupling shoe 271 can be seen. In this figure, only the first axial guide rail 261 is visible. This figure further highlights the fluted coupling hole 21 of the transmission module 2, which is intended to co-operate with the coupling nose 11 of the motor to impart the rotational motion to a transmission shaft, shown in the following figures, and thus constitutes a preferred structural variant for the implementation of the motor coupling part of the transmission module 2.

FIG. 6, which is a sagittal cross-sectional view of the transmission module that can be used in the preferred embodiments of the transmission modules shown in FIGS. 3 and 4, depicts a first longitudinal axis A-A of movement of the cutting tool 3 via the blade holder 27. The rotary motion R of the micromotor 10 is transmitted to a rotatable drive shaft 22, which extends along a second longitudinal axis B-B parallel to the first longitudinal axis A-A. This second longitudinal axis is not shown in this figure for reasons of legibility, but can be seen in particular in FIGS. 7a and 7b described below. The transmission shaft 22 is rotatably mounted between input bearings 28 and output bearings 29, respectively integral with the first part 201 and the second part 202 of the frame 20 of the transmission module 2. In addition, an eccentric 23 configured symmetrically in the shape of a "V" is mounted on this rotating transmission shaft 22. The eccentric 23 comprises a first part 231 on which the first finger 241 is mounted, the reciprocating movement of which drives the blade holder 27, and consequently the cutting tool 3, and a second part 232 on which the second finger 242 is mounted, which is provided for driving the counter-mass 5 in order to achieve the self-balancing of the system. In this figure, the second insertion hole 51 arranged in the counter-mass 5 for the second finger 242 can be clearly seen. In order to be able to transform the rotational movement of the eccentric 23 into a reciprocating movement of the fingers, the body of each of these fingers is also provided with a series of bearings, namely a first series of bearings 251 for the first finger 241, and correspondingly, a second series of bearings 252 for the second finger.

Figure 7B:
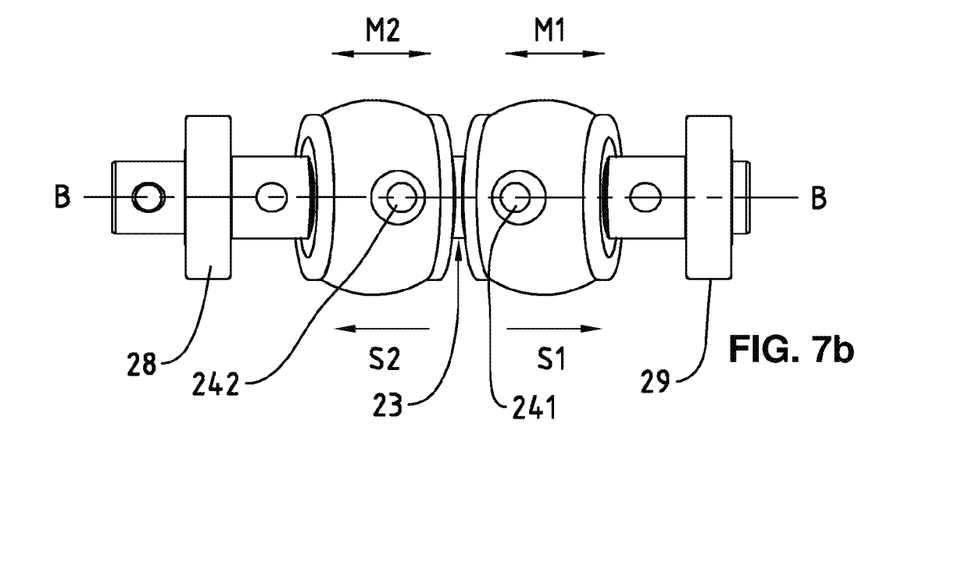

The transmission mechanism, or more precisely, the conversion of the rotary motion applied in input into a reciprocating motion in translation is explained in detail with the aid of FIGS. 7a and 7b, which show respectively a sagittal and a top view of the transmission shaft 22 provided with the eccentric and the fingers mounted on it.

As can be seen in FIG. 7a, the transmission shaft 22 rotates around its axis, i.e. the second longitudinal axis B-B. It is mounted rotatably in relation to the frame 20 via the input bearings 28 in relation to the first part of the frame 201 and the output bearings 29 in relation to the second part 202 of the frame 20 of the transmission module 2. During its rotation, it drives the eccentric 23, whose first part 231 on which the first finger 241 is mounted via the first series of bearings 251 will generate a first reciprocating movement M1 in a first direction S1, whereas the second part on which the second finger 242 is mounted via the second series of bearings 252 will generate a second reciprocating movement M2 with an identical amplitude, but in a direction that is simply opposite (i.e., along the second direction S2). FIG. 7b shows the fingers seen from above; apart from the bearings which are no longer visible inside them, all the elements shown are identical to those in FIG. 7a. This view makes it easy to visualize the translational movement of each of these fingers along the second longitudinal axis B-B and makes it possible to explain why it is more interesting to couple the cutting tool 3, via the blade holder 27, by means of the first finger 241 and to carry out the balancing by means of the counter-mass 5 via the second finger 242. Indeed, since the cutting tool 3 is arranged at the end of the cutter tool, it is more natural to arrange the coupling shoe at this same end, i.e. as far to the right as possible on these figures.

Figure 8:
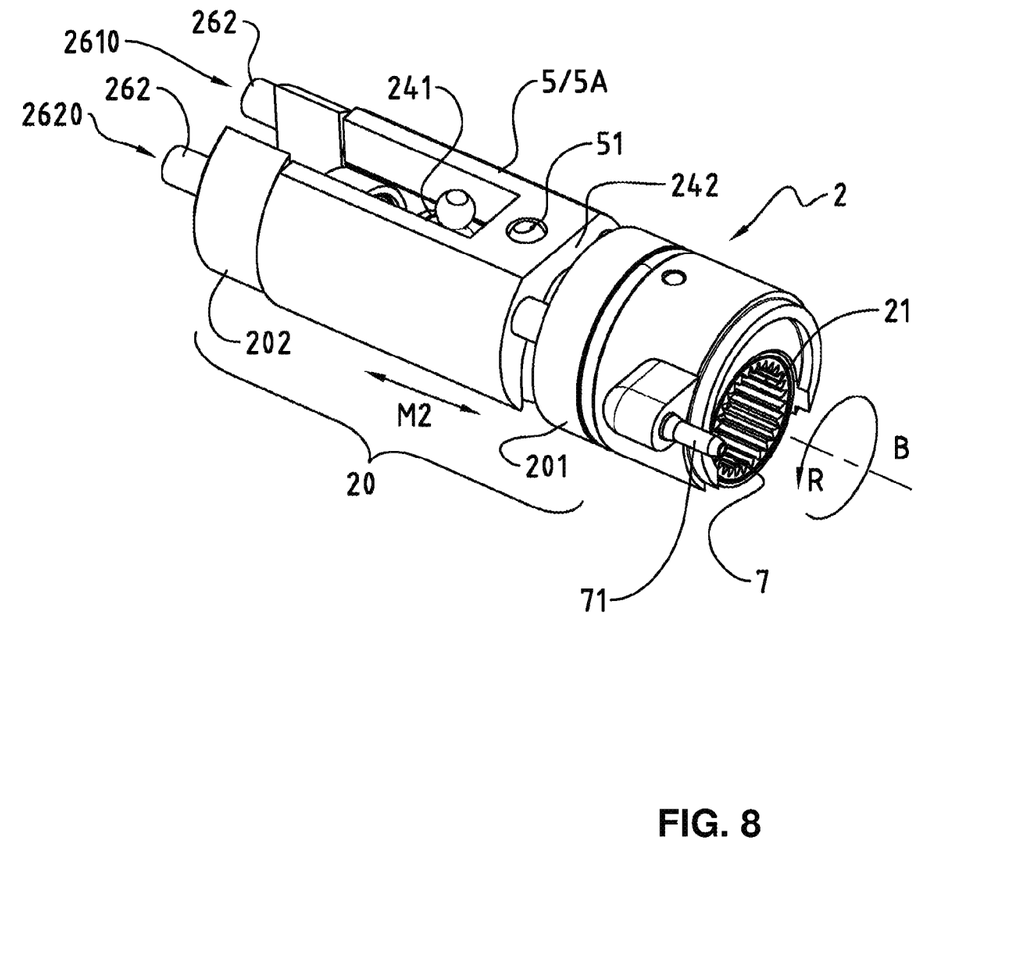
FIG. 8 is a three-dimensional profile view of a transmission module for a cutting tool for surgical or dental use according to a preferred embodiment with a long counter-mass, and which is further provided with an integrated cooling mechanism.

FIG. 8 illustrates a particularly preferred embodiment of a transmission module 2 for carrying out the present invention, the frame 20 of which is provided with an integrated cooling mechanism 7 for the counter-mass 5. According to this illustrated embodiment using a long counter-mass 5A, which aims to achieve the most effective balancing possible of the proposed cutting device in operation, and to best ensure the coupling of the micromotor—not shown in this figure but whose rotational movement R is shown here on the right of FIG. 8—vis-à-vis the handpiece 4 via the coupling hole 21. According to the preferred variant illustrated, the integrated cooling device 7 advantageously uses the longitudinal connecting elements between the first frame part 201 and the second frame part 202, i.e., the cylindrical beams that form axial guide elements 26 in parallel, by incorporating integrated cooling ducts. Thus, as can be seen in dotted lines in FIG. 8, the first axial guide rail 261 is provided with a first integrated cooling duct 2610 and similarly the second axial guide rail 262 is provided with a second integrated cooling duct 2620. A fluid supply duct 71 can thus be directly arranged at the end of the frame close to the micromotor, and can be directly used for a supply of physiological fluid, replacing, for example, the irrigation channel 61 visible especially in FIG. 3. Although according to the preferred embodiment in this figure two channels are used for the cooling ducts, it will be understood that such a configuration is only sufficient, but not necessary for the implementation of the present invention, and that it would also be conceivable to use only a single cooling duct integrated into an axial guide element 26 which would comprise only a single guide rail.

The realization of one or more supply channels inside the guide rails of the counter-mass 5, which thus become irrigation tubes, has two particularly interesting advantages at the operational level:
the irrigation liquid allows the friction zone of the counter-mass 5 to be cooled locally, thus allowing the use of heavier counter-masses—such as the long counter-mass shown in FIG. 8—and therefore longer and heavier surgical blades;

the irrigation of the cutting tool via an internal mechanism avoids the need to connect an irrigation line to the blade holder, as is usually the case a connection of the irrigation line which is therefore made both closer to the surgeon's fingers, and closer to the working area, which also involves a risk of accidental disconnection of the line.

Thus, this solution provides a significant improvement in surgeon ergonomics and patient safety, while providing increased flexibility in calibrating the tool according to the needs.

Still according to a preferred embodiment for the carrying out of the present invention, the weight of the counter-mass 5 is between a minimum value, depending on the motor-workpiece-to-hand disconnection force, the maximum reciprocation frequency of the cutting tool 3, the course D of the cutting tool, as shown in FIG. 3, and the mass of the cutting tool 3—blade holder 27, and a maximum value, depending on the cooling capacity of the micro saw/handpiece 4 and the gripping diameter of the cutting tool. Thus, the weight of the counter-mass is not necessarily equal to the weight of the assembly integral with the cutting tool and which is driven in a reciprocating motion.

These constraints are formulated in the following equation (1), which takes up the fundamental equation of dynamics according to a modeling in conformity with a system materialized according to laws of physics pertaining to the mechanics of the point. In particular, the mass Mc of the counter-mass 5 must be greater than a limit value defined by the following equation (1):

$$x = \frac{\delta}{2}\cos(2\pi f t) \rightarrow \frac{d^2 x}{dt^2} = \frac{\delta}{2}(2\pi f)^2 \cos(2\pi f t) \quad (1)$$

$$a_{max} = 2\delta\pi^2 f^2$$

$$F_d > [M_s + M_p]a_{max} - M_c \, a_{max}$$

$$M_c > M_s + M_p - F_d/2\delta\pi^2 f^2$$

where Ms is the mass of the cutting tool 3, Mp is the mass of the blade holder 27, i.e., the cylindrical body 270 and the coupling shoe 271, Fd is the disconnecting force, δ is the course D of the cutting tool 3, and f is the maximum frequency of the reciprocating motion.

The above equation (1) ensures that the cutting tool 3 is not disconnected from the motor module, i.e. the workpiece corresponding to the micromotor 10, accidentally during the various working situations. For this, the maximum acceleration of the system is calculated and deduced from the equation indicating that the sum of the forces applied to the system is equal to the mass multiplied by the acceleration.

The modeling of the blade holder 27 and cutting tool 3 on the one hand, and the counter-mass 5 on the other hand as material points is justified by the assumption that the solid components are subject to vibrations of very low amplitude, and at high frequency, and therefore their low frequency dynamic behavior is essentially given by the movement of their center of gravity. Since the only active degree of freedom consists of longitudinal movement along the axial guide member 26 (preferably formed by the two axial guide rails 261, 262), there is no rotational drive effect that would require consideration of the position of the center of gravity relative to a possible pivot center.

The mass of the counter-mass 5 must thus be lower than a limit defined by the thermal balance of the micro-saw, without the need to configure a self-balancing system where equivalence (2)

$$M_c = M_s + M_p \quad (2)$$

is strictly respected.

The thermal power generated by the reciprocating movement of the counter-mass 5 on the guide element 26 (such as the first guide rail 261 and the second guide rail 262 parallel to the transmission axis, i.e. the second longitudinal axis B-B) is related in particular to the following factors:

(i) the external surface and material of the micro-saw cap (cooling depending essentially on convection around the handpiece 4);

(ii) the diameter of the handle of the micro-saw, which imposes the maximum diameter of the counter-mass 5 and thus the lever arm between the center of gravity of the counter-mass 5 and the first transmission finger 241 of the reciprocating motion;

(iii) the frequency f and the course D of the reciprocating motion;

(iv) the distance between the axis of the guide rails 261, 262 of the counter-mass 5 and the transmission axis of the reciprocating motion, such as the second longitudinal axis B-B of the transmission shaft 22.

A heavier counterweight, such as for example the long counter-mass 5A, thus makes it possible to better ensure the holding of the micromotor module 10 with the handpiece 4, comprising the transmission module 2. This, however, causes a greater lever arm between its center of gravity and the second transmission finger 242; therefore, to minimize the length of the handpiece 4, it is preferable that the counter-mass 5 occupies all of the free space inside the handle, i.e., the outer casing thereof that is grasped by the dentist. This explains the particular shape of the short counter-mass 5B in FIG. 3 and that of the long counter-mass 5A in FIG. 4, whose cross section corresponds substantially to a truncated cylindrical ring if one disregards the guide holes. Thus, the longer the counter-mass 5 is, the closer its center of gravity is to the central axis of the handle; on the other hand, the end of the second transmission finger 242 driving the counter-mass 5 is preferably as far away as possible from the center of the handpiece 4 in order to maximize the course of the reciprocating movement imposed on the counter-mass 5.

International standards set the maximum temperature that can be reached by the micro-saw (currently 55° C. during normal use), which therefore allows us to deduce the maximum thermal power that can be generated by the presence of the counter-mass 5, which will preferably be made of a metallic material such as bronze, copper, steel or a noble and heavy metal so as to have a density greater than 7,000 kg per cubic meter, and thus make it possible to obtain a sufficient mass without having to require a volume that is too large and cumbersome with respect to the rest of the transmission module, and in particular the kinematic chain for driving the cutting tool 3 itself.

The fact of having, according to the preferred embodiments described with the aid of the preceding figures, counter-masses guided by at least 2 guide rails makes it possible to reduce friction and heating.

According to a particularly advantageous embodiment, the mass of the counter-mass 5 according to the invention is between 25% and 50% of the total mass of the cutting tool 3/blade holder 27 assembly, which further minimizes any additional heating due to self-balancing. Even more preferably, the mass of the counter-mass 5 according to the invention is between 2.5 g and 6 g, while the mass of the cutting tool is between 1 and 3 grams.

Thus, according to the invention, an effective means of counteracting the displacement of the center of mass of a cutting tool with a counter-mass is proposed which:

is independent of the working speed minimizes the dependence on the mass and shape of the micro-saw components to be balanced minimizes the impact on the average efficiency (conversion of rotary motion to reciprocating motion) of the handpiece minimizes the impact on the wear rate of the bearings does not generate overheating of the handpiece allows for a modular physical separation between the mechanical handpiece 4 (the module forming the micro-saw, which does not require a power supply), as shown in FIG. 1, and the power motor, such as the micro-motor 10 also shown in FIG. 1, ensuring that the connection-disconnection of the surgical cutting tool to the motor is simple and fast, thanks to a disconnection force of the order of 30 N (3 kg).

According to the preferred embodiments described, the presence of the counter-mass and a 'symmetrical' transmission system of the rotary motion to the counter-mass and to the blade makes it possible to reduce vibrations. Since the counter-mass moves in perfect phase with the blade, the reduction of vibrations is ensured independently of the rotation speed of the motor. In addition, guiding the counter-mass avoids the heat and wear potentially caused by adding an additional heavy component to the transmission chain. The doubling of the ball bearings for each transmission finger makes it possible to reduce their wear. It is also possible to reduce the inverse dependence of the efficiency with respect to the power applied to the motor (the efficiency decreases with the increase of power for an unbalanced system), thus making it possible to increase the efficiency of cutting.

Although only a few embodiments have been described by way of example in the foregoing, it will be understood, however, that these are not intended to be an exhaustive description of all possible embodiments. One who is skilled in the art will understand that it is conceivable to replace a described means by an equivalent means without departing from the scope of the present invention.

Furthermore, it would also be possible, without going beyond the scope of the present invention, to modify the form of the counter-mass according to the geometry of the cutting tool and the blade holder used, via an electronic or electromagnetic device. A preferred embodiment for implementing such a solution would be, for example, to connect two parts of the counter-mass via an electromagnetic device (of the electromagnet type) positioned on one of the two parts of the counter-mass and a magnet positioned on the second part of the counter-mass. The change of the polarity of the electromagnet thus makes it possible either to bring together (magnetic attraction) or to separate (magnetic repulsion) the two parts of the counter-mass. If a heavier cutting tool is used, the user can force the two parts together ('heavy' counter-mass), whereas if a lighter cutting tool is used, the user can force repulsion between the two parts of the counter-mass, and therefore use a lighter counter-mass.

The invention claimed is:

1. Cutting device for surgical or dental use comprising a motor connected in a removable way to a handpiece provided with a transmission module for a cutting tool, said transmission module comprising:

a motor coupling arranged to be set in rotation by said motor;

a kinematic chain transforming said rotation of the motor into a first linear reciprocating movement of a blade holder via a rotary transmission shaft provided with an eccentric, said transmission module further comprising a counter-mass arranged so as to move according to a second linear reciprocating movement synchronized with said first linear reciprocating movement of said blade holder, and in an opposite direction to the latter.

2. Cutting device for surgical or dental use according to claim 1, wherein the kinematic chain comprises a first drive finger of said blade holder mounted on a first part of said eccentric, as well as a second drive finger of said counter-mass mounted on a second part of said eccentric.

3. Cutting device for surgical or dental use according to claim 2, said eccentric being symmetrically arranged in a "V" shape, said first drive finger of said blade holder being mounted on a first series of bearings around said first part of said eccentric and said second drive finger of said blade holder being mounted on a second series of bearings around said second part of said eccentric.

4. Cutting device for surgical or dental use according to claim 1, wherein a geometric shape of said counter-mass is adapted to that of said cutting tool and said blade holder.

5. Cutting device for surgical or dental use according to claim 1, wherein said counter-mass is guided axially along a first transmission axis corresponding vectorially to a direction of longitudinal displacement of said blade holder and said cutting tool by at least one axial guide element inserted in at least one guide hole made in said counter-mass.

6. Cutting device for surgical or dental use according to claim 5, wherein said axial guide element is formed by a first axial guide rail and a second axial guide rail connecting, in parallel, a first part of a frame connected to said motor to a second part of the frame supporting and axially guiding said blade holder of said transmission module, said first axial guide rail and said second axial guide rail being inserted in respective guide holes of the at least one guide hole of said counter-mass.

7. Cutting device for surgical or dental use according to claim 1, wherein said transmission module further comprises a cooling duct for the counter-mass.

8. Cutting device for surgical or dental use according to claim 7, wherein an axial guide element is formed by a first axial guide rail and a second axial guide rail connecting, in parallel, a first part of a frame connected to said motor to a second part of the frame supporting and axially guiding said blade holder of said transmission module, said first axial guide rail and said second axial guide rail being inserted in respective guide holes of said counter-mass, and wherein the first axial guide rail comprises a first integrated cooling duct and/or said second axial guide rail comprises a second integrated cooling duct.

9. Cutting device for surgical or dental use according to claim 8, wherein said transmission module further comprises a cooling duct for the counter-mass, and wherein a weight of said counter-mass ranges between 25% and 50% of a combined weight of an assembly formed by said blade holder and said cutting tool.

10. Cutting device for surgical or dental use according to claim 7, wherein a density of said counter-mass is greater than 7000 kg per cubic meter.

11. Cutting device for surgical or dental use according to claim 1, wherein said transmission module is detachably connected to said motor, and a weight of said counter-mass is determined so as to be greater than a minimum value defined in relation to a combined weight of an assembly formed by the blade holder and said cutting tool as a function of disconnection force of said transmission module to said motor, of a course of said cutting tool, and of a frequency of oscillation of the reciprocating movement of said cutting tool.

12. Cutting device for surgical or dental use according to claim 1, wherein a weight of said counter-mass is determined so as to be lower than a predefined value determined by a heat balance.

13. Cutting device for surgical or dental use according to claim 1, wherein the motor coupling of said transmission module consists of a fluted coupling hole, which co-operates with a standard coupling nose of said motor comprising a series of grooves into which O-rings are inserted.

14. Handpiece comprising the transmission module for the surgical or dental cutting device according to claim 1.

* * * * *